United States Patent
Minato et al.

(10) Patent No.: US 7,156,829 B2
(45) Date of Patent: Jan. 2, 2007

(54) DISPOSABLE DIAPER HAVING ELASTICIZED WINGS AND WAISTBAND

(75) Inventors: Hironao Minato, Kagawa-ken (JP); Masaki Yoshida, Kagawa-ken (JP); Koichiro Mitsui, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 78 days.

(21) Appl. No.: 10/899,115

(22) Filed: Jul. 27, 2004

(65) Prior Publication Data

US 2005/0027279 A1 Feb. 3, 2005

(30) Foreign Application Priority Data

Jul. 30, 2003 (JP) ............................. 2003-204004

(51) Int. Cl.
*A61F 13/15* (2006.01)
(52) U.S. Cl. .................. 604/385.24; 604/385.01; 604/385.27; 604/385.29
(58) Field of Classification Search ............. 604/358, 604/385.01, 385.24, 385.25, 385.26, 385.27, 604/385.28
See application file for complete search history.

(56) References Cited

U.S. PATENT DOCUMENTS 5,196,000 A * 3/1993 Clear et al. ............. 604/385.29

| | | | |
|---|---|---|---|
| 6,325,787 B1 * | 12/2001 | Roe et al. .............. | 604/385.27 |
| 6,336,922 B1 * | 1/2002 | VanGompel et al. ...... | 604/385.3 |
| 6,448,355 B1 * | 9/2002 | Knight et al. ............ | 526/348 |
| 6,667,351 B1 * | 12/2003 | Langohr et al. .......... | 522/157 |
| 6,692,477 B1 * | 2/2004 | Gibbs ....................... | 604/386 |
| 2001/0018581 A1* | 8/2001 | Minato ..................... | 604/389 |
| 2003/0109844 A1* | 6/2003 | Gibbs ....................... | 604/389 |

FOREIGN PATENT DOCUMENTS

| EP | 1 197 196 A1 * | 4/2002 |
|---|---|---|
| JP | 2000-254176 | 9/2000 |
| JP | 2002/119537 A * | 4/2005 |

* cited by examiner

*Primary Examiner*—Tatyana Zalukaeva
*Assistant Examiner*—Michael G. Bogart
(74) *Attorney, Agent, or Firm*—Lowe Hauptman & Berner LLP

(57) ABSTRACT

A disposable diaper is provided with elastically stretchable waist areas extending in a transverse direction along respective end portions of front and rear waist regions and a pair of elastically stretchable wing areas extending outward in the transverse direction from the side edge portions of the rear waist region. The side edge portions of the rear waist region are respectively interposed between the stretchable waist area and the stretchable wing areas. The stretchable wing areas have a transverse stretch stress higher than a transverse stretch stress of the stretchable waist area, so the tensile force exerted on the stretchable wing areas is segmentalized and restrained by the side edge portions of the rear waist region.

20 Claims, 8 Drawing Sheets

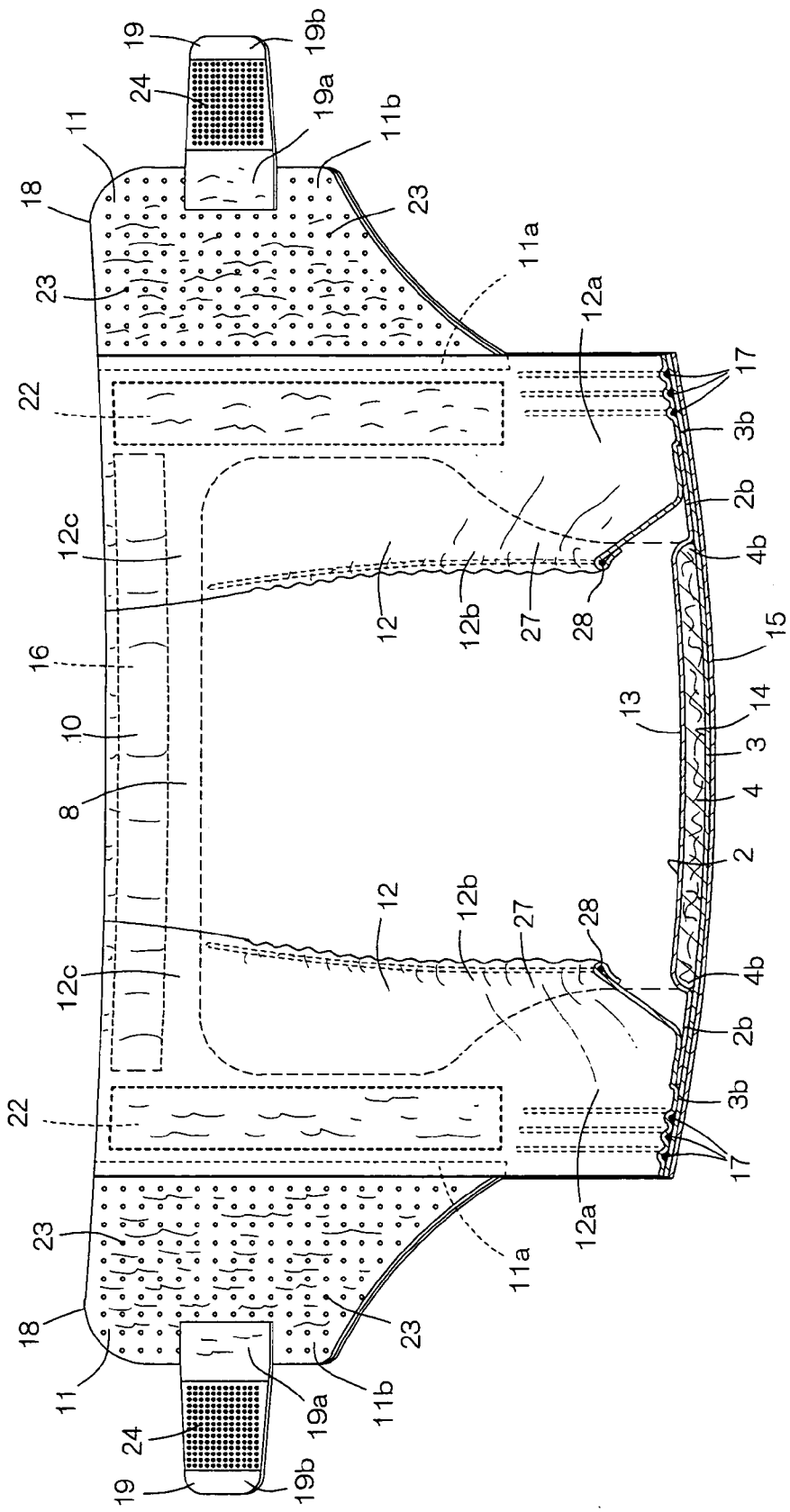

DISPOSABLE DIAPER HAVING ELASTICIZED WINGS AND WAISTBAND

RELATED APPLICATIONS

The present application is based on, and claims priority from, Japanese Application Ser. No. 2003-204004, filed Jul. 30, 2003, the disclosure of which is hereby incorporated by reference herein in its entirety.

BACKGROUND OF THE INVENTION

The present invention relates to a disposable diaper having front and rear waist regions connected to each other by a fastener means when the diaper is put on.

In Japanese Unexamined Patent Application Publication No. 2000-254176 (hereinafter referred to as "Citation"), there has already been proposed a disposable diaper composed of, in a longitudinal direction, a front waist region, a rear waist region and a crotch region extending between these waist regions and comprises a liquid-pervious topsheet, a liquid-impervious backsheet and a liquid-absorbent core interposed between these two sheets. The diaper is contoured by longitudinally opposite ends extending in a transverse direction outside longitudinally opposite ends of the core and transversely opposite side edges extending in the longitudinal direction outside transversely opposite ends of the core and wherein first wings extend outward in the transverse direction from respective side edges of the front waist region and second wings extend outward in the transverse direction from the respective side edges of the rear waist region.

In the diaper disclosed in Citation, band-like first elastic members extending in the transverse direction is contractibly attached to the longitudinally opposite ends of the front and rear waist regions, respectively, and a plurality of strand-like second elastic members extending in the transverse direction are contractibly attached to the rear waist region so as to lie between the end of the core and the first elastic member in the rear waist region. In this diaper, the second elastic members extend between the transversely opposite side edge portions and further into wings. The wings of the rear waist region are elastically stretchable in the transverse direction. Each of the tape fasteners has a fixed portion permanently bonded to the associated wing of the rear waist region and a free portion extending outward from the fixed portion in the transverse direction. Hooks constituting a so-called mechanical fastener are attached to the free portion of the tape fastener and a stretch stress higher than those of the inner layer sheet and the outer layer sheet. Each of the tape fastener has a fixed side portion which is permanently bonded to outer end of the associated second wing and a free portion extending outward from the fixed side portion in the transverse direction. Hooks constituting a so-called mechanical fastener are attached to the free portion.

An example of the sequence in accordance with which a parent or a care personnel puts the diaper on the wearer's body will be described. After the hip of the wearer lying face up has been laid on the developed diaper, the front waist region is held with the hand and folded back along the crotch region onto the wearer's belly. Then, with the tape fasteners gripped by the fingers, the wings of the rear waist region are folded back so that these wings are placed on respective outer sides of the wings of the front waist region. Adjusting a tightness of the end portions as well as of the wings around the wearer's waist, the free portions of the respective tape fasteners are alternately anchored on the outer surface of the front waist region. Upon connection of the front and rear waist regions to each other, the diaper is formed with a waist-hole and a pair of leg-holes.

In the case of the diaper disclosed in Citation, the second elastic members are stretched in the transverse direction and thereby the wings of the rear waist region also are stretched in the transverse direction as the tape fasteners are pulled outward in the transverse direction when the diaper is put on. A tensile force exerted on the second elastic members is transmitted to the first elastic member which is, in turn, stretched in the transverse direction and thereby the end portion of the rear waist region is stretched in the transverse direction.

In this diaper, the first and second elastic members may often different stretch stresses since the first elastic members are band-like and the second elastic members are strand-like. With a consequence, a transverse stretch stress of the end portion of the rear waist region along which the first elastic member extends may often be different from a transverse stretch stress of the wings of the rear waist region along which the second elastic members extend.

If the wings of the rear waist region exhibit a transverse stretch stress higher than a transverse stretch stress exhibited by the end of the rear waist region, the end of the rear waist region will be fully stretched before the wings should be sufficiently stretched. If the free portions of the respective tape fasteners are anchored on the front waist region at this moment, the diaper will be put on the wearer's body with the wings insufficiently stretched in the transverse direction. Consequently, the contractile force of the wings can not be utilized to ensure a desired tightness of the diaper around the waist of the wearer and the diaper may slip down from the proper position at which the diaper should be held on the wearer's body. In addition, the end portion of the rear waist region may locally constrict the wearer's waist and the wearer may experience uncomfortable feeling of local oppression.

SUMMARY OF THE INVENTION

It is an object of the present invention to provide a disposable diaper improved so as to prevent the diaper from slipping down during its use and to give the wearer no uncomfortable feeling of local oppression around the wearer's waist.

According to the present invention, there is provided a disposable diaper composed of a front waist region, a rear waist region, a crotch region extending between these two waist regions and comprising a liquid-pervious topsheet facing the wearer's skin, a liquid-impervious backsheet facing away from the wearer's skin and a liquid-absorbent core interposed between these top- and backsheets, the diaper being contoured by longitudinally opposite end portions extending in a transverse direction outside longitudinally opposite ends of the core and transversely opposite side edge portions extending in a longitudinal direction outside transversely opposite side edges of the core wherein said front and rear waist regions are connected to each other by means of a fastening means when the diaper is put on.

The diaper according to the present invention further comprises the following features.

Of the front and rear waist regions, at least the rear waist region includes an elastically stretchable waist area extending in the transverse direction along its end and elastically stretchable wing areas extending outward from its transversely opposite side edge portions in the transverse direction wherein the transversely opposite side edge portions of the rear waist region lie between the stretchable waist area and the stretchable wing areas and the stretchable wing areas have a transverse stretch stress higher than that of the stretchable waist area.

According to one preferred embodiment of the invention, the stretchable elasticity of the elastically stretchable waist area is created by a first elastic member contractibly attached to the waist region along its end and the stretchable elasticity of the elastically stretchable wing areas is created by stretchy sheets separately of the top- and backsheets.

According to another preferred embodiment of the invention, the elastically stretchable waist area presents a transverse stretch stress in a range of 0.5 to 3.0 N as a first transverse length dimension of the elastically stretchable waist area is stretched to a first transverse length dimension corresponding to 90% of its maximally stretched transverse length dimension set as 100%, each of the elastically stretchable wing areas presents a transverse stretch stress in a range of 1.5 to 7.0 N as each of the elastically stretchable wing areas is stretched to a second transverse length dimension corresponding to 120% of its non-stretched transverse length dimension set as 100% and presents a transverse stretch stress in a range of 3.0 to 10.0 N as each of the elastically stretchable wing areas is stretched to a second length dimension corresponding to 150% of its non-stretched transverse length dimension set as 100%.

According to still another preferred embodiment of the invention, the transversely opposite side edge portions of the rear waist region are substantially non-stretchable.

According to further another preferred embodiment of the invention, second elastic members contractibly attached to the transversely opposite side edge portions of the rear waist region make the transversely opposite side edge portion stretchable in the transverse direction and the transverse stretch stress of the elastically stretchable wing areas is lower than the transverse stretch stress of the transversely opposite side edge portions of the rear waist region.

According to an additional preferred embodiment of the invention, the transversely opposite side edge portions of the rear waist region present a transverse stretch stress in a range of 5 to 20 N as the side edge portions are stretched to a third length dimension corresponding to 90% on the basis of their maximally stretched transverse length dimension set as 100%.

BRIEF DESCRIPTION OF THE DRAWINGS

FIG. 8 is a sectional view taken along the line VIII—VIII in FIG. 5.

DETAILED DESCRIPTION OF THE PREFERRED EMBODIMENTS

Details of a disposable diaper according to the present invention will be more fully understood from the description given hereunder with reference to the accompanying drawings.

Figure 1:
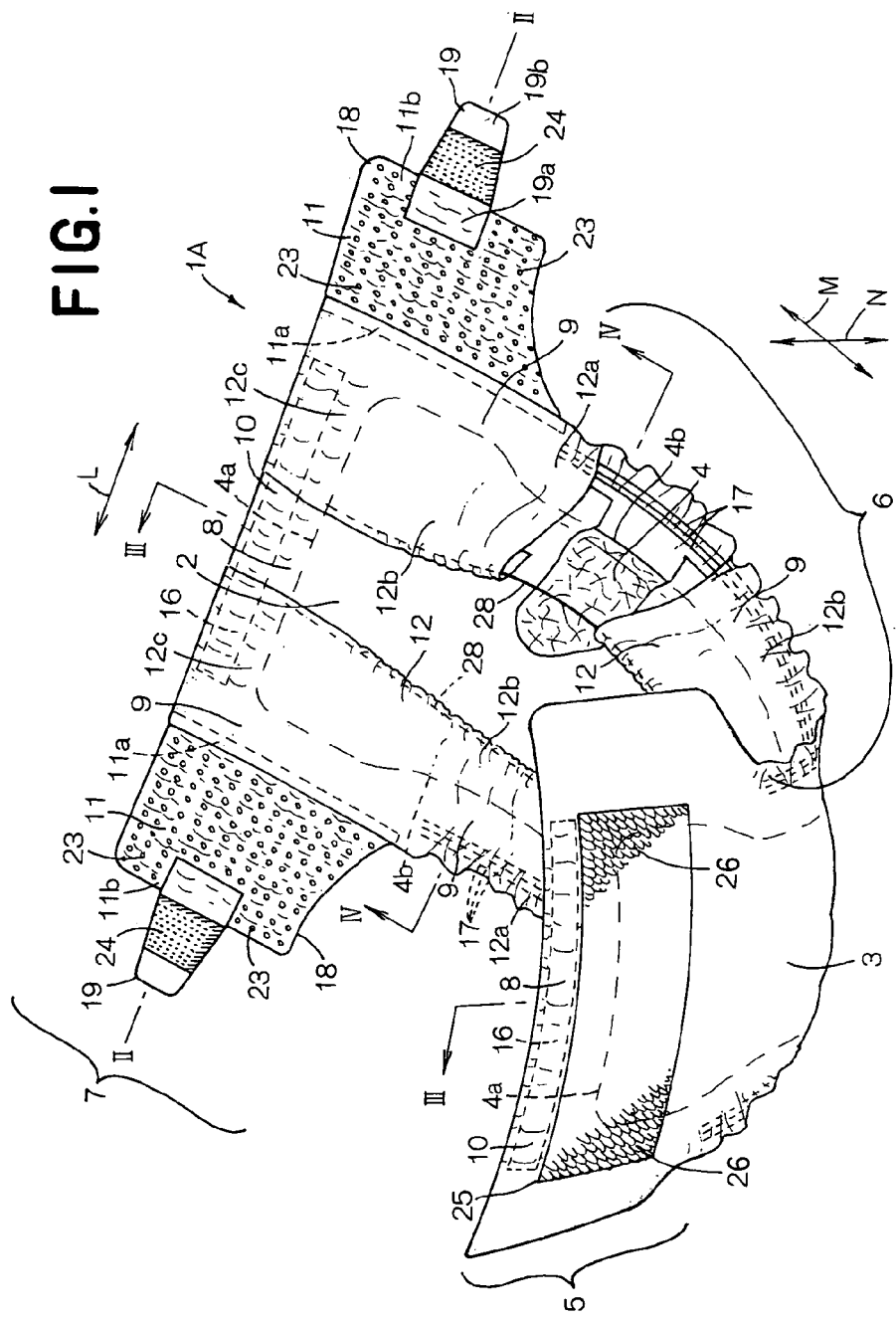
FIG. 1 is a partially cutaway perspective view showing a diaper as an embodiment of the invention.
Figure 2:
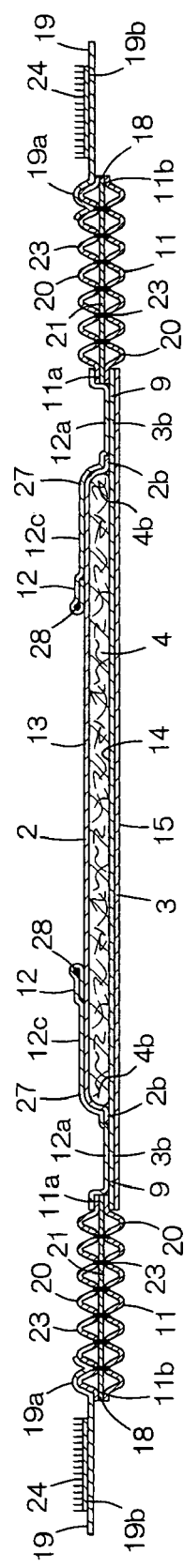
FIG. 2 is a sectional view taken along the line II—II in FIG. 1.
Figure 3:
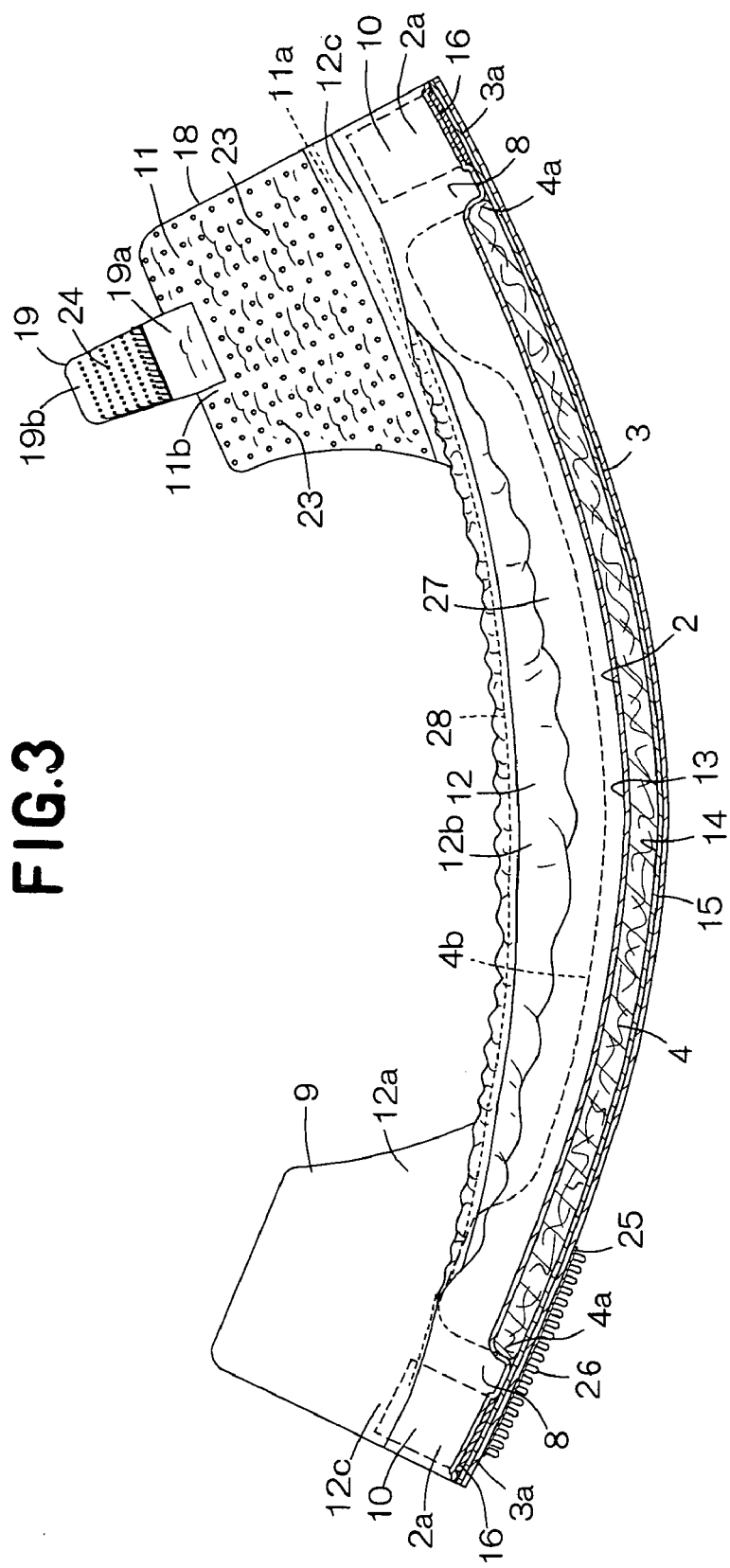
FIG. 3 is a sectional view taken along the line III—III in FIG. 1.
Figure 4:
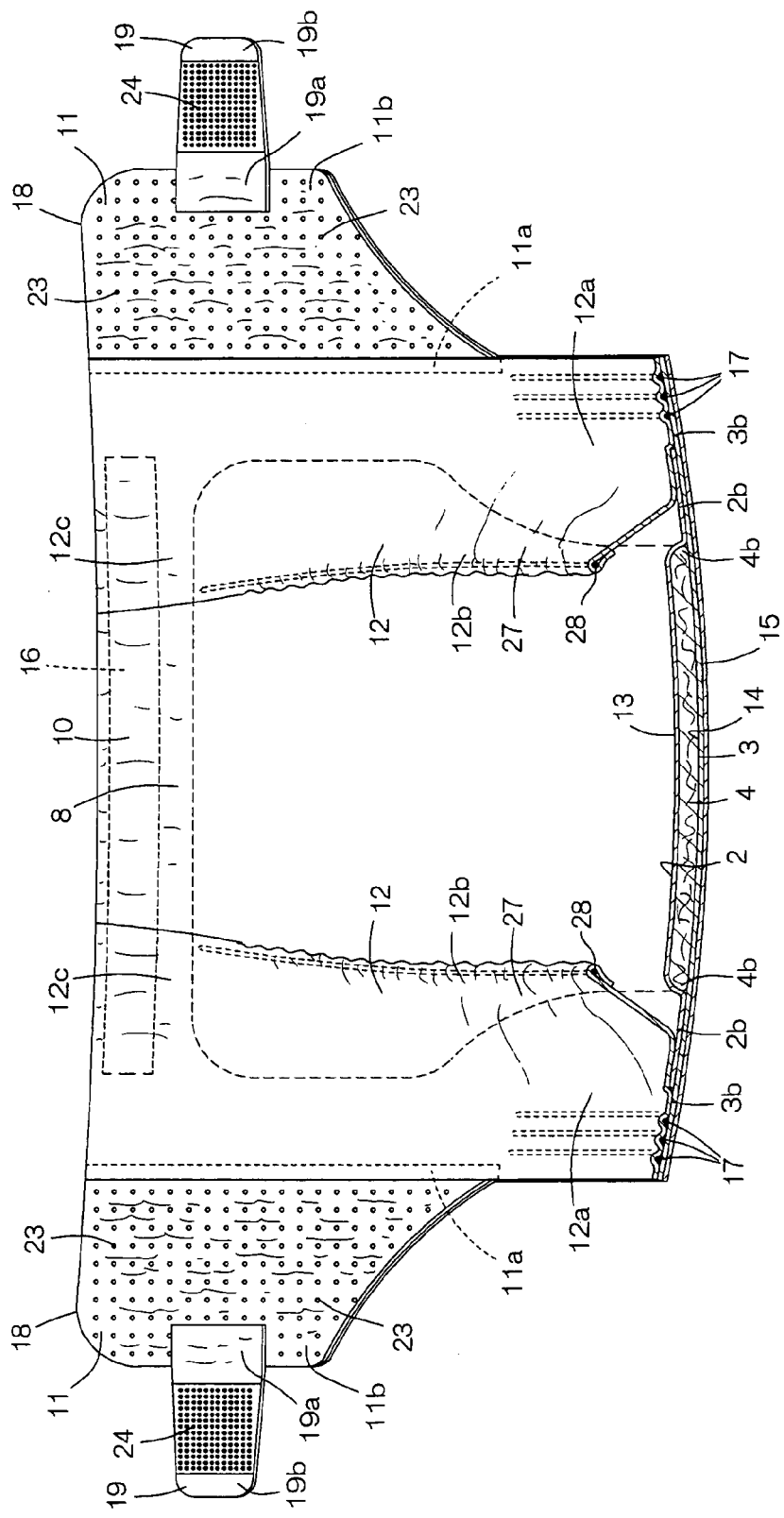
FIG. 4 is a sectional view taken along the line IV—IV in FIG. 1.

FIG. 1 is a perspective view showing an open-type diaper 1A, one of embodiments of the invention, as partially broken away, FIG. 2 is a sectional view taken along the line II—II in FIG. 1, FIG. 3 is a sectional view taken along the line III—III in FIG. 1 and FIG. 4 is a sectional view taken along the line IV—IV in FIG. 1. In FIG. 1, a transverse direction is indicated by an arrow L and a longitudinal direction is indicated by an arrow M. As used here, the phrase "inner surfaces" of top- and backsheets and leak-barrier sheets refers to surfaces thereof facing an absorbent core and as used here, the phrase "outer surfaces" of these sheets refers to surfaces thereof facing away from an absorbent core. As used here, the phrase "skin contacting side" refers to the side facing the wearer's skin and as used here, the phrase "skin non-contacting side" refers to the side facing away from the wearer's skin.

A diaper 1A basically comprises a liquid-pervious topsheet 2 lying on a skin contacting side, a liquid-impervious backsheet 3 lying on the skin non-contacting side and a liquid-absorbent core 4 interposed between the top- and backsheets 2, 3. The diaper 1A is composed, in the longitudinal direction, a front waist region 5, a rear waist region 7 and a crotch region 6 extending between these waist regions 5, 7 wherein the diaper 1A is contoured by longitudinally opposite end portions 8 extending in the transverse direction across the front and rear waist regions 5, 7 outside longitudinally opposite ends 4a of the core 4 and transversely opposite side edge portions 9 extending in the longitudinal direction between the front and rear waist regions 5, 7 outside transversely opposite ends 4b of the core 4.

The diaper 1A further includes elastically stretchable waist areas 10 defined by the respective end portions 8 of the front and rear waist regions 5, 7 and a pair of elastically stretchable wing areas 11 extending outward in the transverse direction from the side edge portions 9 of the rear waist region 7. A transverse length dimension between the side edge portions 9 is larger in the front waist region 5 than in the crotch region 6 and thus the diaper 1A presents a substantially hourglass-like planar shape. A pair of leak-barrier sheets 12 are attached to the side edge portions 9 so as to extend in the longitudinal direction.

The topsheet 2 is formed from a breathable hydrophilic fibrous nonwoven fabric 13. The backsheet 3 is formed from a breathable liquid-impervious plastic film 14 and a breathable hydrophobic fibrous nonwoven fabric 15 placed upon each other so that the film 14 lies on the skin contacting side and the nonwoven fabric 15 lies on the skin non-contacting side. The film 14 and the nonwoven fabric 15 have respective surfaces opposed to each other and intermittently bonded to each other by means of adhesive (not shown). The core 4 extends over the crotch region 6 further into the front and rear waist regions 5, 7 and is permanently bonded to at least one of inner surfaces of the topsheet 2 and the backsheet 3.

The core 4 comprises a mixture of particulate or fibrous super-absorbent polymer and fluff pulp or a mixture of particulate or fibrous super-absorbent polymer, fluff pulp and thermoplastic synthetic resin fiber, in any case, compressed to a desired thickness. Preferably, the core 4 is entirely wrapped with a liquid-pervious sheet such as a tissue paper or hydrophilic fibrous nonwoven fabric in order to avoid a possibility that the core 4 might get out of its initial shape and/or the particulate polymer might fall off from the core 4. The polymer may be selected from the group consisting of starch-based polymer, cellulose-based polymer and synthetic polymer.

The longitudinally opposite end portions 8 are formed from longitudinally opposite end portions 2a of the topsheet 2 and longitudinally opposite end portions 3a of the backsheet 3 extending outward beyond longitudinally opposite ends 4a of the core 4. The top- and backsheets 2, 3 are overlapped together along the end portions 2a, 3a thereof and inner surfaces of these sheets 2, 3 are permanently bonded together to form the respective end portions 8. Elasticity of the stretchable waist areas 10 is created by tape-like first elastic members 16 (i.e., waist-surrounding elastic members) contractibly attached to the respective end portions 8 of the front and rear waist regions 5, 7. The first elastic members 16 are interposed between the respective end portions 2a of the topsheet 2 and the respective end portions 3a of the backsheet 3 and are permanently and intermittently bonded to the inner surfaces of these sheets 2, 3 by means of adhesive (not shown). The first elastic members 16 are permanently bonded to the top- and backsheets 2, 3 while the first elastic members 16 are stretched in the transverse direction at a given ratio. In the stretchable waist areas 10, the top- and backsheets 2, 3 shrink in the transverse direction as the elastic members 16 contract and thereupon these sheets 2, 3 are formed with a plurality of gathers rising and falling in a thickness direction of the diaper 1A.

The transversely opposite side edge portions 9 are formed from transversely opposite side edge portions 2b of the topsheet 2, transversely opposite side edge portions 3b of the backsheet 3 and respective fixed side portions 12a (as will be described later in details) of the leak-barrier sheets 12 extending outward in the transverse direction beyond transversely opposite side edges 4b of the core 4. Along the side edge portions 9, the side edge portions 2b of the topsheet 2 extend outward in the transverse direction slightly beyond the transversely opposite side edges 4b of the core 4 and the side edge portions 3b of the backsheet 3 as well as the side edge portions 12a of the leak-barrier sheets 12 extend outward in the transverse direction beyond the side edge portions 2b of the topsheet 2. Along the side edge portions 9, the respective side edge portions 2b, 3b, 12a of these sheets 2, 3, 12 are overlapped together and have inner and outer surfaces thereof permanently bonded together. The side edge portions 9 are substantially non-stretchable. The side edge portions 9 of the rear waist region 7 lie between the stretchable waist area 10 and the stretchable wing areas 11.

A plurality of string-like leg surrounding elastic members 17 are contractibly attached to the respective side edge portions 9 of the crotch region 6 so as to extend in the longitudinal direction. More specifically, the leg surrounding elastic members 17 are interposed between the respective side edge portions 3b of the backsheet 3 and the respective fixed side portions 12a of the leak-barrier sheets 12 and are intermittently and permanently bonded to the inner surfaces of these sheets 3, 12 by means of adhesive (not shown) while these elastic members 17 are stretched in the longitudinal direction at a given ratio. Along the side edge portions 9, the backsheet 3 and the leak-barrier sheets 12 shrink in the longitudinal direction as the elastic members 17 contract and these sheets 3, 12 are formed with a plurality of gathers rising and falling in the thickness direction of the diaper 1A.

The stretchable wing areas 11 are formed from an elastically stretchable sheet 18 which are prepared separately of the top- and backsheets 2, 3 as well as the leak-barrier sheets 12 and elastically stretchable in the transverse direction. The stretchable wing areas 11 have a transverse stretch stress higher than that of the stretchable waist areas 10. The stretchable wing areas 11 have transversely inner end portions 11a interposed between the side edge portions 3b of the backsheet 3 and the fixed side portions 12a of the leak-barrier sheets 12 and permanently bonded to respective inner surfaces of these sheets 3, 12 by means of adhesive (not shown). A pair of tape fasteners 19 (fastening means) extending in the transverse direction are attached to the transversely outer end portions 11b of the respective stretchable wing areas 11.

The stretchable sheet 18 comprises a pair of breathable hydrophobic fibrous nonwoven fabric layers 20 and breathable liquid-impervious stretchy plastic film 21 sandwiched between these nonwoven fabric layers 20. These nonwoven fabric layers 20 are formed with a plurality of gathers rising and falling in the thickness direction of the diaper 1A.

The elastically stretchable sheet 18 may be obtained, for example, by placing and bonding the nonwoven fabric layers 20 on and to both surfaces of the stretchy plastic film 20 which is under a tension in the transverse direction. Upon relaxation, the film 21 contracts in the transverse direction and a contractile force of the film 21 causes the nonwoven fabric layers 20 to shrink in the transverse direction and to be formed with the gathers. Specifically, the nonwoven fabric layers 20 and the film 21 have respective surfaces opposed one to another overlap and intermittently bonded one to another at a plurality of heat-sealing spots rather evenly distributed in a dotted pattern. For bonding of the nonwoven fabric layers 20 to the film 21 may be achieved using welding technique such as heat-sealing or sonic sealing. Alternatively, the nonwoven fabric layers 20 and the film 21 may be intermittently bonded together using adhesive instead of using the heat-sealing spots 23.

The fibrous nonwoven fabric 20 is formed from polyolefin-based thermoplastic synthetic resin fiber. The polyolefin-based thermoplastic synthetic resin may be selected from the group consisting of polyamide-, polyester-, polyethylene-, polypropylene-based thermoplastic synthetic resin. The plastic film 21 is formed by thermoplastic synthetic resin having rubber-like elasticity. The thermoplastic synthetic resin forming the film 21 is made of material selected from the group consisting of styrene-based block copolymer, polyurethane-based block copolymer, polyester-based block copolymer, polyamide-based block copolymer and copolymer blend. The styrene-based block copolymer may be selected from a group consisting of styrene-butadiene-styrene (S-B-S) and styrene-ethylene butadiene-styrene (S-EB-S). The copolymer blend may be selected from the group consisting of styrene-ethylene butadiene-styrene/polypropylene (S-EB-S/PP) and polypropylene/ethylene-propylene (PP/-P).

Alternatively, the stretchable sheet 18 may be formed from a single layer of the breathable hydrophobic fibrous nonwoven fabric 20 and the stretchy plastic film 21. In this case, the nonwoven fabric layer 20 may be placed and bonded on and to one surface of the stretchy plastic film 21 being stretched in the transverse direction by means of the heat-sealing spots 23 or by means of adhesive.

Each of the tape fasteners 19 has a fixed side portion 19a permanently bonded to the outer end portion 11b of the associated second stretchable wing area 11 by means of adhesive (not shown) and a free portion 19b extending outward from the fixed side portion 19a in the transverse direction. Stock material for the tape fastener 19 may be selected from the group consisting of a fibrous nonwoven fabric made of polyolefin-based thermoplastic synthetic resin fiber and a film made of polyolefin-based thermoplastic resin. The free portion 19b is provided with a plurality of hooks 24 extending in the thickness direction of the diaper 1A. These hooks 24 are made of polyolefin-based thermoplastic synthetic resin. Alternatively, the free portion 19b may be coated with pressure-sensitive adhesive, instead of the hooks 24.

The front waist region 5 is provided with a target tape 25 (fastening means) on which the free end portions 19b of the respective tape fasteners 19 are releasably anchored. The target tape 25 has a rectangular shape having its longer sides extending in the transverse direction and is intermittently or continuously bonded to the outer surface of the backsheet 3 by means of adhesive (not shown). Stock materials for this target tape 25 may be selected from the group consisting of a fibrous nonwoven fabric made of polyolefin-based thermoplastic synthetic resin fiber and a plastic film made of polyolefin-based thermoplastic synthetic resin. The target tape 25 is provided on its outer surface with a plurality of loops 26 each describing a circular arc in the thickness direction of the diaper 1A. These loops 26 are made of polyolefin-based thermoplastic synthetic resin. When it is desired to coat the free portions 19b of the respective tape fasteners 19 with pressure-sensitive adhesive, the synthetic resin film may be used as the target tape 25.

The leak-barrier sheets 12 are formed from a breathable hydrophobic fibrous nonwoven fabric 27. The leak-barrier sheets 12 respectively have the fixed side portions 12a extending between the front and rear waist regions 5, 7 in the longitudinal direction along the side edge portions 9, a movable portions 12b normally biased to rise up above the topsheet 2 and extending between the front and rear waist regions 5, 7 in the longitudinal direction and longitudinally opposite fixed end portions 12c lying on the longitudinally opposite end portions 8, respectively, and collapsed inward in the transverse direction of the diaper 1A. Elastic members 28 extending in the longitudinal direction are contractibly attached to the movable portions 12b in the vicinity of distal ends of these movable portions 12b wherein each of the elastic members 28 is wrapped with a part of the movable portion 12b and intermittently and permanently bonded to the movable portions 12b by means of adhesive (not shown). The fixed end portions 12c are permanently bonded to the outer surface of the respective end portions 2a of the topsheet 2. In the leak-barrier sheets 12, the elastic members 28 contract as the diaper 1A is curved in the longitudinal direction with the topsheet 2 inside and a contractile force of these elastic members 28 causes the movable portions 12b to rise up above the topsheet 2 so as to form barriers against bodily discharges.

An example of the sequence in accordance with which a parent or a care personnel puts the diaper 1A on the wearer's body will be described. After the hip of the wearer lying face up has been laid on the developed diaper 1A, the front waist region 5 is held with the hand and folded back along the crotch region 6 onto the wearer's belly. Then, with the free portions 19b of the tape fasteners 19 gripped by the fingers, the stretchable wing areas 11 are folded back so that these stretchable wing areas 11 may be positioned above the wearer's belly. Adjusting a tightness of the stretchable waist area 10 as well as the stretchable wing areas 11 around the wearer's waist by stretching the wing areas 11 in the transverse direction, the free portions 19b of the respective tape fasteners 19 are anchored on the outer surface of the target tape 25 and thereby the front and rear waist regions 5, 7 are connected to each other.

To anchor the tape fasteners 19 on the target tape 25, the free portions 19b of the respective tape fasteners 19 may be pressed against the outer surface of the target tape 25 and thereby the hooks 24 may be engaged with the loops 26. Upon connection of the front and rear waist regions 5, 7 to each other, the diaper 1A is formed with a waist-hole and a pair of leg-holes (not shown). Excretion discharged on the diaper 1A put on the wearer's body is absorbed by the core 4 through the topsheet 2 and contained therein.

The stretchable wing areas 11 are stretched in the transverse direction as the tape fasteners 19 pulled outward in the transverse direction and a tensile force exerted on the stretchable wing areas 11 is transmitted to the side edge portions 9 of the rear waist region 7 defined between the stretchable waist area 10 and the stretchable wing areas 11. Even when the tensile force exerted on the stretchable wing areas 11 is transmitted to the side edge portions 9 of the rear waist region 7, such tensile force is segmentalized and restrained by the substantially non-stretchable side edge portions 9 and the tensile force transmitted from the stretchable wing areas 11 to the stretchable waist area 10 can be reduced. Therefore, while the waist area 10 having a stretch stress lower than that of the wing areas 11 is stretched in the transverse direction in the course of stretching the wing areas 11, it is unlikely that the stretchable waist area 10 might be fully stretched before the stretchable wing areas 11 are sufficiently stretched in the transverse direction. In this way, the free portions 19b of the respective tape fasteners 19 can be anchored on the target tape 25 with the stretchable waist area 10 as well as the stretchable wing areas 11 sufficiently stretched.

A parent or a care personnel is able to put the diaper 1A on the wearer's body with not only the stretchable waist area 10 but also the stretchable wing areas 11 sufficiently stretched. In other words, there is no anxiety that the diaper 1A might be put on the wearer's body with the stretchable wing areas 11 insufficiently stretched. In this way, it is ensured that the diaper 1A can be appropriately tightened around the wearer's waist by utilizing a contractile force of the stretchable waist area 10 as well as a contractile force of the stretchable wing areas 11. The diaper 1A can be held in close contact with the wearer's skin along the end portions 8 as well as the side edge portions 9 of the front and rear waist regions 5, 7 to avoid both the apprehension that the end portions 8 and/or the side edge portions 9 might shift from the proper positions and the apprehension that the diaper 1A might slip down from the proper position.

The diaper 1A is free from the anxiety that the stretchable waist area 10 might locally compress the wearer's waist and the wearer might experience uncomfortable feeling of local oppression around the waist. Even if the stretchable waist area 10 of the front waist region 5 constrict the wearer's waist, such constriction is not so significant that the wearer might be prevented from his or her abdominal respiration and might experience uncomfortable feeling to wear the diaper 1A.

The elastically stretchable waist area 10 presents a transverse stretch stress in a range of 0.5 to 3.0 N as this elastically stretchable waist area 10 is stretched to its first transverse length dimension corresponding to 90% of its maximally stretched transverse length dimension set as 100%, each of the elastically stretchable wing areas 11 presents a transverse stretch stress in a range of 1.5 to 7.0 N as each of the elastically stretchable wing areas 11 is stretched to its second transverse length dimension corresponding to 120% of its non-stretched transverse length dimension set as 100% and presents a transverse stretch stress in a range of 3.0 to 10.0 N as each of the elastically stretchable wing areas 11 is stretched to its second length dimension corresponding to 150% of its non-stretched transverse length dimension set as 100%.

If the stretch stress of the wing areas 11 exceeds the above-mentioned higher limit values, an excessively high tensile force will be required to stretch the wing areas 11 in the transverse direction and, in consequence, it will be impossible to control a tensile force transmitted from the stretchable wing areas 11 to the stretchable waist area 10. Thus undesirably high tensile force may be transmitted from the stretchable wing areas 11 to the stretchable waist area 10 and the stretchable waist area 10 may be fully stretched in the transverse direction before the stretchable wing areas 11 are sufficiently stretched. In this case, the diaper 1A may be put on with the stretchable wing areas 11 insufficiently stretched in the transverse direction.

If the stretch stress of the stretchable waist area 10 is less than the above-mentioned lower limit values, the stretchable waist area 10 will be fully stretched under a relatively low tensile force and, as an inevitable result, it will be impossible to put the diaper 1A on the wearer's body with the stretchable wing areas 11 sufficiently stretched. Additionally, a contractile force of the stretchable waist area 10 will be substantially ineffective and it will be impossible for the stretchable waist area 10 to clinch the wearer's waist appropriately. If the stretch stress of the stretchable waist area 10 exceeds the above-mentioned higher limit values and the stretch stress of the stretchable wing areas 11 is less than the above-mentioned lower limit values, the stretchable waist area 10 will needlessly clinch the wearer's waist, leading to a feeling of local oppression and sometimes making an abdominal respiration difficult. At the same time, the contractile force of the stretchable wing areas 11 is substantially ineffective to clinch the wearer's waist appropriately by these stretchable wing areas 11.

The stretch stress of the stretchable waist area 10 was measured using a method as follows:

(1) The stretchable waist area 10 (including the first elastic members) is cut away from the end portion 8 of the rear waist region 7 to prepare a first sample having a transverse dimension of 220 to 240 mm for measurement of stretch stress. INSTRON 5543 or AUTOGRAPH manufactured by INSTRON JAPAN CO. is used to measure the stretch stress.

(2) One end of the first sample in the transverse direction is held by an upper chuck and the other end of the first sample in the transverse direction is held by a lower chuck. A length dimension of the sample measured between the upper and lower chucks is 125 mm. The first sample is now stretched in the vertical direction at a rate of 100 mm/min so that the upper and lower chucks may get away from each other.

(3) On the basis of a length dimension of the first sample having been stretched to the maximum limit as measured between the upper and lower chucks set as 100%, the first sample is stretched to a length dimension corresponding to 90% and a stretch stress at this moment is measured as the transverse stretch stress of the stretchable waist area 10.

The stretch stress of the stretchable wing areas 11 was measured using a method as follows:

(1) The transversely opposite side edge portions 9 of the rear waist region 7 are cut away from the diaper 1A to prepare second samples for measurement of stretch stress. Each sample comprises a part of the side edge portion 9 and the complete stretchable wing area 11 (including the tape fastener 19). INSTRON 5543 or AUTOGRAPH manufactured by INSTRON JAPAN CO. is used to measure the stretch stress.

(2) A fixture is attached to the side edge portion 9 of the sample except the stretchable wing area 11 so that the fixture may extend along full length of the side edge portion 9. Of the second sample, the tape fastener 19 is held by an upper chuck and the fixture is held by a lower chuck. A length dimension of the sample measured between the upper and lower chucks is 70 mm.

(3) A length dimension of the non-stretched second sample extending between the upper and lower chucks without slacks is set as 100%. The second sample is stretched in the vertical direction at a rate of 100 min/min so that the upper and lower chucks may get away from each other. The second sample is stretched to a length dimension corresponding to 120% of its non-stretched length and a stretch stress of the second sample at this moment is measured and then the second sample is stretched to a length dimension corresponding to 150% of its non-stretched length and a stretch stress of the second sample at this moment is measured.

Figure 5:
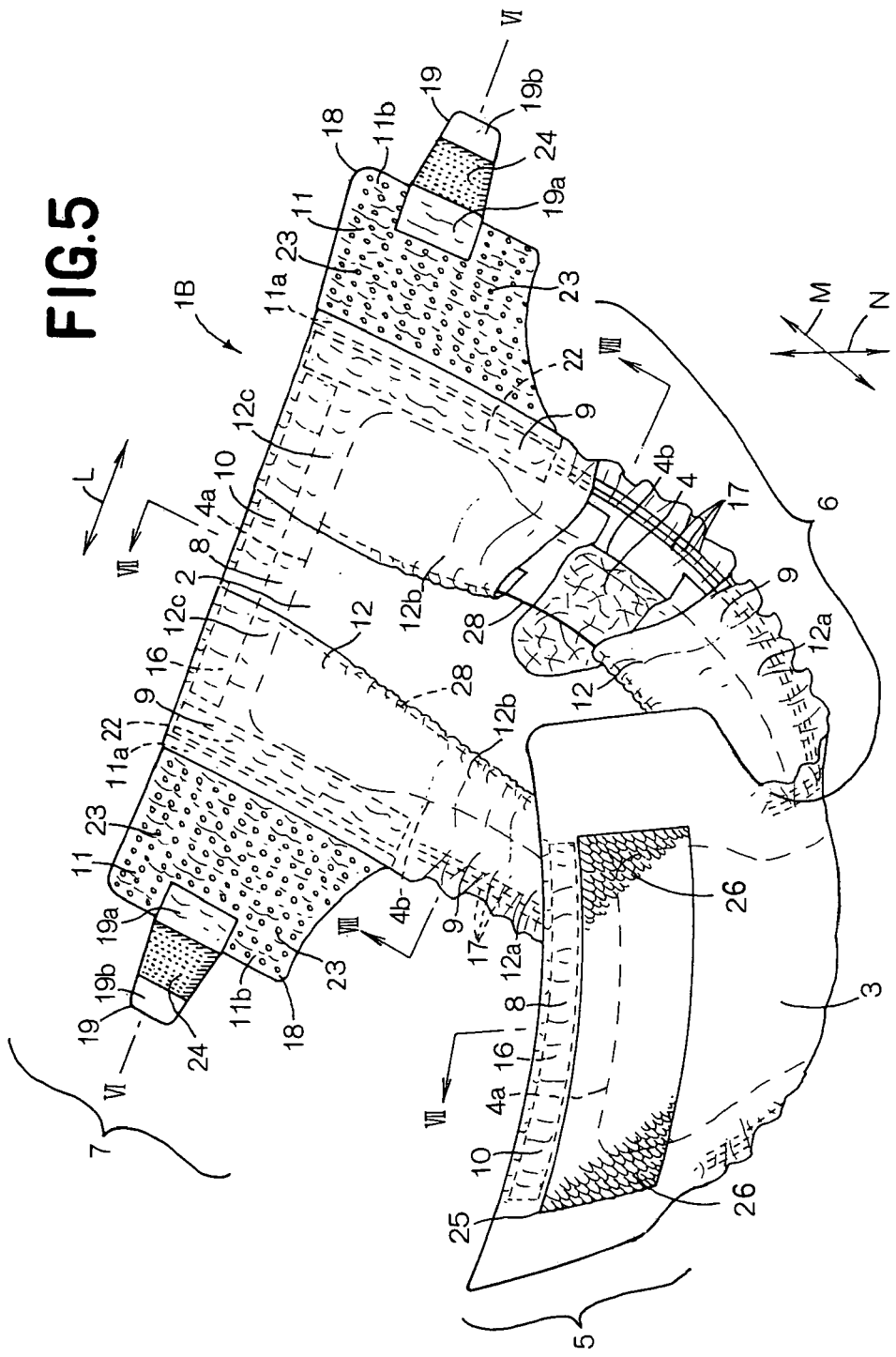
FIG. 5 is a partially cutaway perspective view showing another embodiment of the invention.
Figure 6:
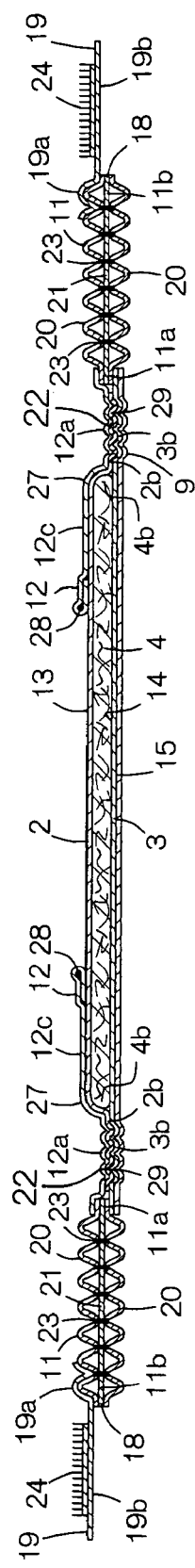
FIG. 6 is a sectional view taken along the line VI—VI in FIG. 5.
Figure 7:
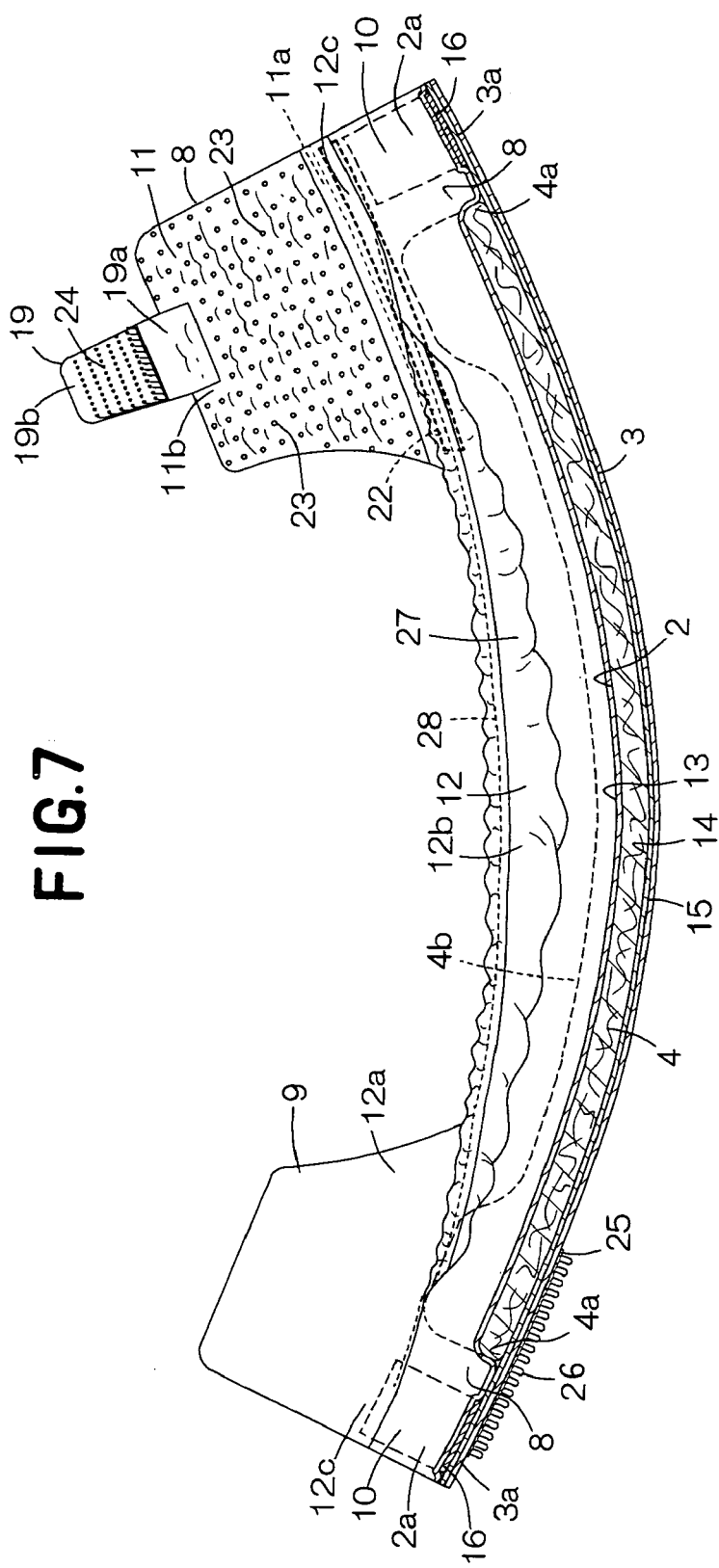
FIG. 7 is a sectional view taken along the line VII—VII in FIG. 5.

FIG. 5 is a partially cutaway perspective view showing a diaper 1B as another embodiment of the invention, FIG. 6 is a sectional view taken along the line VI—VI in FIG. 5, and FIGS. 7 and 8 are sectional views taken along lines VII—VII and VIII—VIII, respectively. In FIG. 5, the transverse direction is indicated by an arrow L, the longitudinal direction is indicated by an arrow M and the thickness direction is indicated by an arrow N.

The diaper 1B basically comprises a liquid-pervious topsheet 2, a liquid-impervious backsheet 3 and a liquid-absorbent core 4 interposed between the top- and backsheets 2, 3. The diaper 1B is composed of, in the longitudinal direction, a front waist region 5, a rear waist region 7 and a crotch region 6 extending between these waist regions 5, 7. The diaper 1B is contoured by longitudinally opposite end portions 8 extending across the front and rear waist regions 5, 7 in the transverse direction outside longitudinally opposite ends 4a of the core 4 and transversely opposite side edge portions 9 extending between the front and rear waist regions 5, 7 in the longitudinal direction outside transversely opposite side edges 4b of the core 4.

The diaper 1B further includes elastically stretchable waist areas 10 defined by the respective end portions 8 of the front and rear waist regions 5, 7 and a pair of elastically stretchable wing areas 11 extending outward in the transverse direction from the side edge portions 9 of the rear waist region 9. A pair of leak-barrier sheets 12 extending in the longitudinal direction are attached to the side edge portions 9. The topsheet 2 is formed by the same nonwoven fabric 13 as that of the diaper 1A and the backsheet 3 is formed from the film 14 and the nonwoven fabric 15 both being the same as those of the diaper 1A. The core 4 also is the same as that of the diaper 1A.

The longitudinally opposite end portions 8 are formed from longitudinally opposite end portions 2a of the topsheet 2 and longitudinally opposite end portions 3a of the backsheet 3 extending outward beyond longitudinally opposite ends 4a of the core 4. The top- and backsheets 2, 3 are overlapped together along the end portions 2a, 3a thereof. Elasticity of the stretchable waist areas 10 is created by tape-like first elastic members 16 (i.e., waist-surrounding elastic members) contractibly attached to the respective end portions 8 of the front and rear waist regions 5, 7. The first elastic members 16 are interposed between the respective end portions 2a of the topsheet 2 and the respective end portions 3a of the backsheet 3 and are permanently and intermittently bonded to the inner surfaces of these sheets 2, 3. In the stretchable waist areas 10, the top- and backsheets 2, 3 shrink in the transverse direction as the elastic members 16 contract and thereupon these sheets 2, 3 are formed with a plurality of gathers rising and falling in a thickness direction of the diaper 1B.

The transversely opposite side edge portions 9 are formed from transversely opposite side edge portions 2b of the topsheet 2, transversely opposite side edge portions 3b of the backsheet 3 and the respective fixed side portions 12a of the leak-barrier sheets 12 extending outward in the transverse direction beyond transversely opposite side edges 4b of the core 4. Along the side edge portions 9, the respective side edge portions 2b, 3b, 12a of these sheets 2, 3, 12 are overlapped together and have inner and outer surfaces thereof permanently bonded together.

The transversely opposite side edge portions 9 of the rear waist region 7 are elastically stretchable in the transverse direction and interposed between the stretchable waist area 10 and the stretchable wing areas 11. Elasticity of the side edge portions 9 are created by second elastic members 22 contractibly attached thereto. The second elastic members 22 present substantially rectangular shape having its longer sides extending in the longitudinal direction. These second elastic members 22 are interposed between the side edge portions 3b of the backsheet 3 and the fixed side portions 12a of the respective leak-barrier sheets 12 and intermittently and permanently bonded to the respective inner surfaces of these sheets 3, 12 by means of adhesive (not shown). The second elastic members 22 are bonded to the backsheet 3 and the leak-barrier sheets 12 while the second elastic members 22 are stretched in the transverse direction at a given ratio. Along the side edge portions 9, the backsheet 3 and the leak-barrier sheets 12 shrink in the longitudinal direction as the elastic members 17 contract and these sheets 3, 12 are formed with a plurality of gathers rising and falling in the thickness direction of the diaper 1B.

A plurality of string-like leg surrounding elastic members 17 are contractibly attached to the respective side edge portions 9 of the crotch region 6 so as to extend in the longitudinal direction. More specifically, the leg surrounding elastic members 17 are interposed between the respective side edge portions 3b of the backsheet 3 and the respective fixed side portions 12a of the leak-barrier sheets 12 and are intermittently and permanently bonded to the inner surfaces of these sheets 3, 12 while these elastic members 17 are stretched in the longitudinal direction at a given ratio. Along the side edge portions 9 of the crotch region 6, the backsheet 3 and the leak-barrier sheets 12 shrink in the longitudinal direction as the elastic members 17 contract and these sheets 3, 12 are formed with a plurality of gathers rising and falling in the thickness direction of the diaper 1B.

The stretchable wing areas 11 are formed from an elastically stretchable sheet 18 which are prepared separately of the top- and backsheets 2, 3 as well as the leak-barrier sheets 12 and elastically stretchable in the transverse direction. The stretchable wing areas 11 have a transverse stretch stress which is higher than that of the stretchable waist areas 10 and lower than that of the side edge portions 9 in the rear waist region 7. The stretchable wing areas 11 have transversely inner end portions 11a interposed between the side edge portions 3b of the backsheet 3 and the fixed side portions 12a of the leak-barrier sheets 12 and permanently bonded to respective inner surfaces of these sheets 3, 12. Inner end portion 11a of the stretchable wing area 11 has substantially the same longitudinal dimension as that of the second elastic members 22 attached to the side edge portions 9 of the rear waist region 7. A pair of tape fasteners 19 (fastening means) extending in the transverse direction are attached to the transversely outer end portions 11b of the respective stretchable wing areas 11. The stretchable sheet 18 comprises, similarly to that of the diaper 1A, a pair of breathable hydrophobic fibrous nonwoven fabric layers 20 and breathable, liquid-impervious and stretchy plastic film 21 sandwiched therebetween. The nonwoven fabric layers 20 and the film 21 are intermittently bonded together at a plurality of heat-sealing spots distributed in dot-pattern.

Each of the tape fasteners 19 has a fixed side portion 19a permanently bonded to the outer end portion 11b of the associated second stretchable wing area 11 and a free portion 19b extending outward from the fixed side portion 19a in the transverse direction. The free portion 19b is provided with a plurality of hooks 24 extending in the thickness direction of the diaper 1B. The tape fasteners 19 and hooks 24 are made of the same materials as those used in the embodiment of the diaper 1A.

The front waist region 5 is provided with a target tape 25 (fastening means) on which the free end portions 19b of the respective tape fasteners 19 are releasably anchored. The target tape 25 has a rectangular shape having its longer sides extending in the transverse direction and is permanently bonded to the outer surface of the backsheet 3. The target tape 25 is provided on its outer surface with a plurality of loops 26 each describing a circular arc in the thickness direction of the diaper 1B. The target tape 25 and the loops 26 are made of the same materials as those used in the embodiment of the diaper 1A.

The leak-barrier sheets 12 are formed from the same nonwoven fabric 27 as that used in the embodiment of the diaper 1A. The leak-proof sheets 12 respectively have the fixed side portions 12a extending between the front and rear waist regions 5, 7 in the longitudinal direction along the side edge portions 9, a movable portions 12b normally biased to rise up above the topsheet 2 and extending between the front and rear waist regions 5, 7 in the longitudinal direction and longitudinally opposite fixed end portions 12c lying on the longitudinally opposite end portions 8, respectively, and collapsed inward in the transverse direction of the diaper 1B. Elastic members 28 extending in the longitudinal direction are contractibly attached to the movable portions 12b in the vicinity of distal ends of these movable portions 12b. The fixed end portions 12c are permanently bonded to outer surface of the respective end portions 2a of the topsheet 2. The movable portions 12b rise up above the topsheet 2 so as to form barriers against bodily discharges.

The sequence in which a parent or a care personnel puts the diaper 1B on the wearer's body is the same as in the case of the diaper 1A and not described here to eliminate duplication. The stretchable wing areas 11 are stretched in the transverse direction as the tape fasteners 19 pulled outward in the transverse direction with the free portions 19b gripped by the fingers and a tensile force exerted on the stretchable wing areas 11 is transmitted to the side edge portions 9 of the rear waist region 7 defined between the stretchable waist area 10 and the stretchable wing areas 11. Even when the tensile force exerted on the stretchable wing areas 11 is transmitted to the side edge portions 9 of the rear waist region 7, such tensile force is segmentalized and restrained by the substantially non-stretchable side edge portions 9 and the tensile force transmitted from the stretchable wing areas 11 to the stretchable waist area 10 can be reduced. Therefore, while the waist area 10 having a stretch stress lower than that of the wing areas 11 is stretched in the transverse direction in the course of stretching the wing areas 11, it is unlikely that the stretchable waist area 10 might be fully stretched before the stretchable wing areas 11 are sufficiently stretched in the transverse direction. In this way, the free portions 19*b* of the respective tape fasteners 19 can be anchored on the target tape 25 with the stretchable waist area 10 as well as the stretchable wing areas 11 sufficiently stretched.

A parent or a care personnel is able to put the diaper 1B on the wearer's body with not only the stretchable waist area 10 but also the stretchable wing areas 11 sufficiently stretched. In other words, there is no anxiety that the diaper 1B might be put on the wearer's body with the stretchable wing areas 11 insufficiently stretched. In this way, it is ensured that the diaper 1B can be appropriately tightened around the wearer's waist by utilizing a contractile force of the stretchable waist area 10 as well as a contractile force of the stretchable wing areas 11. The diaper 1B can be held in close contact with the wearer's skin along the end portions 8 as well as the side edge portions 9 of the front and rear waist regions 5, 7 to avoid both the apprehension that the end portions 8 and/or the side edge portions 9 might shift from the proper positions and the apprehension that the diaper 1B might slip down from the proper position.

The diaper 1B is free from the anxiety that the stretchable waist area 10 might locally compress the wearer's waist and the wearer might experience uncomfortable feeling of local oppression around the waist. Even if the stretchable waist area 10 of the front waist region 5 constrict the wearer's waist, such constriction is not so significant that the wearer might be prevented from his or her abdominal respiration and might experience uncomfortable feeling to wear the diaper 1B.

In the diaper 1B, the elastically stretchable waist area 10 presents a transverse stretch stress in a range of 0.5 to 3.0 N as the elastically stretchable waist area 10 is shortened to a transverse length dimension corresponding to 90% of a second length dimension if the stretchable waist area 10 as maximally stretched in the transverse direction and set as 100%, each of the elastically stretchable wing areas 11 presents a transverse stretch stress in a range of 1.5 to 7.0 N as each of the elastically stretchable wing areas 11 is stretched to a length dimension corresponding to 120% of a second length dimension of the wing areas 11 non-stretched in the transverse direction and set as 100% and presents a transverse stretch stress in a range of 3.0 to 10.0 N as each of the elastically stretchable wing areas 11 is stretched to a length dimension corresponding to 150% of a second length dimension of the wing-areas 11 non-stretched in the transverse direction and set as 100%.

In the diaper 1B, the side edge portion 9 of the rear waist region 7 presents a transverse stretch stress in a range of 5 to 20 N as a third length dimension of the side edge portion 9 is shortened to 90% of the third length dimension of the side edge portion maximally stretched in the transverse direction and set as 100%.

The stretch stress of the elastically stretchable waist area 10 and the stretch stress of the stretchable wing areas 11 were measured using the methods as have been described in connection with the embodiment of the diaper 1A. The stretch stress of the side edge portions 9 in the rear waist region 7 was measured by a method as follows:

(1) The transversely opposite side edge portions 9 (including the second elastic members 22) of the rear waist region 7 are cut away from the diaper 1B to prepare third samples each having transverse dimension of 10 to 50 mm for measurement of stretch stress. INSTRON 5543 or AUTOGRAPH manufactured by INSTRON JAPAN CO. is used to measure the stretch stress.

(2) One lateral end of the third sample is held by an upper chuck and the opposite lateral end thereof is held by a lower chuck. A length dimension of the sample measured between these two chucks is 10 mm. The third sample is pulled in the vertical direction at a rate of 100 mm/min so that the upper and lower chucks may get away from each other.

(3) The third sample is stretched to a length dimension corresponding to 90% of the length dimension of the third sample maximally stretched, measured between the two chucks and set as 100%. At this moment, a stretch stress of the third sample is measured as the transverse stretch stress of the side edge portions 9 in the rear waist region 7.

Stock materials for the topsheet 2 may be selected from the group consisting of a hydrophobic fibrous nonwoven fabric having a plurality of apertures and a plastic film having a plurality of fine perforations. Stock materials for the backsheet 3 may be selected from the group consisting of a breathable hydrophobic fibrous nonwoven fabric, a breathable liquid-impervious plastic film and a composite nonwoven fabric comprising two or more breathable hydrophobic fibrous nonwoven fabric layers laminated one upon another. Stock materials for the leak-barrier sheets 12 may be selected from the group consisting of a composite nonwoven fabric comprising two or more breathable hydrophobic fibrous nonwoven fabric layers laminated one upon another and a composite sheet comprising a breathable hydrophobic fibrous nonwoven fabric and a breathable liquid-impervious plastic film laminated upon each other.

As stock materials for the backsheet 3 and the leak-barrier sheets 12, it is also possible to use a composite nonwoven fabric (SM nonwoven fabric or SMS nonwoven fabric) consisting of a melt blown fibrous nonwoven fabric having a high water-resistance and a spun bond fibrous nonwoven fabric having a high strength as well as a high flexibility laminated on at least one side of the melt blown fibrous nonwoven fabric.

Fibrous nonwoven fabric used to form the top- and backsheets 2, 3, the leak-barrier sheets 12, the stretchable wing areas 11, the tape fasteners 19 and the target tape 25 may be selected from those obtained by spun lace-, needle punch-, melt blown-, thermal bond-, spun bond- and chemical bond-processes.

The hydrophilic fibrous nonwoven fabric may be made of any one of synthetic fiber, semi-synthetic fiber and regenerated fiber each modified to become hydrophilic or conjugate fiber thereof. The hydrophobic fibrous nonwoven fabric may be formed from synthetic fiber and may contain therein semi-synthetic fiber or regenerated fiber both treated to become water repellent. While not specified, the synthetic fiber may be selected from the group consisting of polyester-, polyacrylonitrile-, polyvinyl chloride-, polyethylene-, polypropylene- and polystyrene-based fibers. The suitably useful synthetic fibers further include core-sheath type conjugate fiber, side-by-side type conjugate fiber, macaroni fiber, microporous fiber and bonded-type conjugate fiber.

It is preferred to use hot melt adhesive as the adhesive. In addition to hot melt adhesive, it is also possible to use any one of acrylic adhesive and elastomeric adhesive. The adhesive may be applied on the top- and backsheets 2, 3 and the leak-barrier sheets 12 in a suitable pattern selected from the group consisting of a spiral pattern, zigzag pattern, dotted pattern and striped pattern. Application of the adhesive on these sheets 2, 3, 12 in such pattern generates adhesive-coated regions and adhesive-free regions, resulting in that these sheets 2, 3, 12 are permanently bonded one to another in intermittent fashion, the sheets 2, 3, 12 are bonded to one to another in an intermittent fashion and the core 4 is permanently bonded to the sheets 2, 3 and the elastic members 16, 17, 22, 28 are also bonded to the sheets 2, 3, 12 in an intermittent fashion.

In these diapers 1A, 1B having been described in reference with the accompanying drawings, the stretchable waist area 10 may be formed along the end portion 8 of at least the rear waist region 7 of the front and rear waist regions 5, 7. The first and second elastic members 16, 22 may be provided in the form of strand-like elastic members. As stock materials for the first and second elastic members 16, 22, the leg surrounding elastic members 17 and the elastic members 28, it is also possible to use natural rubber, synthetic rubber or urethane foam.

The disposable diaper according to the present invention is characterized in that the tensile force exerted on the stretchable wing areas is segmentalized and restrained by the side edge portions of the rear waist region which are respectively interposed between the stretchable waist area and the stretchable wing areas so as to reduce the tensile force transmitted to the stretchable waist area. In this diaper, the stretchable waist area having a stretch stress lower than that of the stretchable wing areas is stretched in the transverse direction in the course of stretching the stretchable wing areas. However, there is no possibility that the stretchable waist area might be fully stretched in the transverse direction before the stretchable wing areas are stretched, so the diaper can be put on the wearer's body with the stretchable wing areas sufficiently stretched in the transverse direction. In addition, the contractile force of the stretchable wing areas and the stretchable waist area is effectively utilized to ensure, that the diaper can appropriately constrict the wearer s waist and it is possible to prevent the diaper from slipping down from the proper position. This diaper is free from the anxiety that the stretchable waist area might locally constrict and the wearer might experience uncomfortable feeling of local oppression.

In the case of the diaper wherein the side edge portions of the rear waist region are elastically stretchable and these side edge portions have a transverse stretch stress higher than a transverse stretch stress, even if the tensile force exerted on the stretchable wing areas is transmitted to the side edge portions of the rear waist region, such tensile force is segmentalized and restrained by the side edge portions of the rear waist region having a stretch stress higher than that of the stretchable wing areas. Consequently, the tensile force transmitted to the stretchable waist area can be reduced. In the course of stretching the stretchable wing areas, the stretchable waist area having a stretch stress lower than that of the stretchable wing areas is stretched in the transverse direction. However, there is no anxiety that the stretchable waist area might be fully stretched before the stretchable wing areas are stretched in the transverse direction. Namely, the diaper can be put on the wearer's body with the stretchable wing areas sufficiently stretched in the transverse direction. This diaper allows the contractile force of the stretchable wing areas and the stretchable waist area to be effectively utilized to ensure that the diaper can reliably constrict the wearer's waist and unintentional slip down of the diaper from the proper position can be prevented.

What is claimed is:

1. A disposable diaper, comprising:
   a front waist region;
   a rear waist region;
   a crotch region extending between these said waist regions;
   a liquid-pervious topsheet facing the wearer's skin;
   a liquid-impervious backsheet facing away from the wearer's skin;
   a liquid-absorbent core interposed between said top- and backsheets;
   said diaper being contoured by longitudinally opposite end portions extending in a transverse direction outside longitudinally opposite ends of said core and transversely opposite side edge portions extending in a longitudinal direction outside transversely opposite side edges of said core wherein said front and rear waist regions are connected to each other by means of fastening means when the diaper is put on; and
   of said front and rear waist regions, at least said rear waist region including an elastically stretchable waist area extending in the transverse direction along its end and elastically stretchable wing areas extending outward from its transversely opposite side edge portions in the transverse direction, said transversely opposite side edge portions of said rear waist region lying between said stretchable waist area and said stretchable wing areas and said stretchable wing areas having a transverse stretch stress higher than that of said stretchable waist area;
   wherein second elastic members contractibly attached to the transversely opposite side edge portions of said rear waist region make said transversely opposite side edge portion stretchable in the transverse direction and the transverse stretch stress of said elastically stretchable wing areas is lower than the transverse stretch stress of the transversely opposite side edge portions of said rear waist region.

2. The diaper according to claim 1, further comprising
   a first elastic member contractibly attached to said rear waist region along the longitudinal end portion of said diaper in said rear waist region, wherein the stretchable elasticity of said elastically stretchable waist area is created by said first elastic member; and
   said elastically stretchable wing areas comprise stretchy sheets different from said topsheet and backsheet, wherein the stretchable elasticity of said elastically stretchable wing areas is created by said stretchy sheets.

3. The diaper according to claim 1, wherein
   said elastically stretchable waist area presents a transverse stretch stress in a range of 0.5 to 3.0 N as said elastically stretchable waist area is stretched in the transverse direction to 90% of a maximally stretchable transverse dimension of said elastically stretchable waist area,
   each of said elastically stretchable wing areas presents a transverse stretch stress in a range of 1.5 to 7.0 N as each of said elastically stretchable wing areas is stretched in the transverse direction to 120% of a non-stretched transverse dimension of said elastically stretchable wing area, and
   each of said elastically stretchable wing areas presents a transverse stretch stress in a range of 3.0 to 10.0 N as each of the elastically stretchable wing areas is stretched in the transverse direction to 150% of said non-stretched transverse dimension of said elastically stretchable wing area.

4. The diaper according to claim 1, wherein the transversely opposite side edge portions of said rear waist region present a transverse stretch stress in a range of 5 to 20 N as said side edge portions are stretched in the transverse direction to 90% of a maximally stretchable transverse dimension of said side edge portions.

5. The diaper according to claim 1, wherein said second elastic members have first and second dimensions measured in the longitudinal and transverse directions of said diaper, respectively, and the first dimension is greater than the second dimension.

6. The diaper according to claim 5, wherein, in a transverse cross section taken perpendicular to the longitudinal direction of said diaper, each of said second elastic members is positioned between and completely spaced from (a) a respective one of the transversely opposite side edges of said core and (b) a respective one of said wing areas.

7. The diaper according to claim 6, further comprising:
a first elastic member contractibly attached to said rear waist region along an end of said rear waist region, wherein the stretchable elasticity of said elastically stretchable waist area is created by said first elastic member; and
said elastically stretchable wing areas comprise stretchy sheets different from said topsheet and backsheet, wherein the stretchable elasticity of said elastically stretchable wing areas is created by said stretchy sheets;
wherein, in said transverse cross section, each of said second elastic members is further positioned between and completely spaced from (a) one of terminal ends of said first elastic member, and (b) the respective one of said wing areas.

8. The diaper according to claim 1, further comprising leg elastics being different from said second elastic members and extending along edges of the transversely opposite side edge portions of said diaper;
wherein each of said second elastic members is located on an imaginary extension of at least one of said leg elastics.

9. The diaper according to claim 8, wherein said second elastic members are entirely sandwiched between the topsheet and the backsheet.

10. A disposable diaper, comprising:
a front waist region;
a rear waist region;
a crotch region extending in a longitudinal direction of said diaper between said front and rear waist regions;
a liquid-pervious topsheet adapted to face a wearer's skin;
a liquid-impervious backsheet adapted to face away from the wearer's skin;
a liquid-absorbent core interposed between said topsheet and backsheet;
two wing portions each of which have an inner end attached to one of transversely opposite side portions of the rear waist region, and an outer end extending in a transverse direction of said diaper outwardly from said inner end, wherein said wing portions are elastically stretchable in said transverse direction;
fastening elements which are located at the outer ends of said wing portions for attaching the front and rear waist regions together;
a rear waist elastic which is elongated in the transverse direction, is attached to an end portion of the rear waist region, and defines in said rear waist region a waist band elastically stretchable in said transverse direction; and
two elastic members each of which is elongated in the longitudinal direction, is attached to one of the transversely opposite side portions of the rear waist region and renders said transversely opposite side portion elastically stretchable in said transverse direction;
wherein, in a transverse cross section taken perpendicular to the longitudinal direction of said diaper, each of said elastic members is positioned between (a) one of terminal ends of said rear waist elastic and (b) one of said wing portions; and
wherein said wing portions are less stretchable in the transverse direction than said waist band, and are more stretchable in the transverse direction than the transversely opposite side portions of said rear waist region.

11. The diaper according to claim 10, wherein said wing portions have a transverse stretch stress in the transverse direction higher than that of said waist band, and lower than that of the transversely opposite side portions of said rear waist region.

12. The diaper according to claim 11, wherein
the transverse stretch stress of said waist band is in a range of 0.5 to 3.0 N as said waist band is stretched in the transverse direction to 90% of a maximally stretchable transverse dimension of said waist band;
the transverse stretch stress of each of said wing portions is in a range of 1.5 to 7.0 N as said wing portion is stretched in the transverse direction to 120% of a non-stretched transverse dimension of said wing portion;
the transverse stretch stress of each of said wing portions is in a range of 3.0 to 10.0 N as said wing portion is stretched in the transverse direction to 150% of said non-stretched transverse dimension of said wing portion; and
the transverse stretch stress of each of transversely opposite side edge portions of said rear waist region is in a range of 5 to 20 N as said side edge portion is stretched in the transverse direction to 90% of a maximally stretchable transverse dimension of said side edge portion.

13. The diaper according to claim 10, further comprising leg elastics which are different from said elastic members, extend in the longitudinal direction, and are contractibly attached along edges of transversely opposite side edge portions of at least said crotch region.

14. The diaper according to claim 13, wherein each of said elastic members has a dimension in the transverse direction greater than that of each of said leg elastics.

15. The diaper according to claim 14, wherein each of said elastic members is located on imaginary extensions of two of said leg elastics.

16. The diaper according to claim 13, wherein each of said elastic members is entirely spaced in the longitudinal direction from rearmost ends of said leg elastics.

17. The diaper according to claim 16, wherein each of said elastic members is located on an imaginary extension of at least one of said leg elastics.

18. The diaper according to claim 10, wherein, in said transverse cross section, each of said elastic members is positioned between and completely spaced in the transverse direction from (a) an adjacent one of transversely opposite side edges of said core and (b) an innermost end of the respective one of said wing portions, said innermost end being sandwiched between the topsheet and the backsheet.

19. The diaper according to claim 17, wherein, in said transverse cross section, each of said elastic members is further completely spaced in the transverse direction from (a) the adjacent one of the terminal ends of said rear waist elastic and (b) the respective one of said wing portions.

20. The diaper according to claim 13, wherein said elastic members are entirely sandwiched between the topsheet and the backsheet.

* * * * *